US006770179B1

(12) United States Patent
Nanci

(10) Patent No.: US 6,770,179 B1
(45) Date of Patent: Aug. 3, 2004

(54) BIOSENSORS COMPRISING A COVALENTLY ATTACHED MONOMOLECULAR BIOLOGICAL CONJUGATE LAYER AND A TRANSDUCING DEVICE

(75) Inventor: Antonio Nanci, Dollard-des-Ormeaux (CA)

(73) Assignee: Universite de Montreal, Quebec (CA)

( * ) Notice: Subject to any disclaimer, the term of this patent is extended or adjusted under 35 U.S.C. 154(b) by 0 days.

(21) Appl. No.: 09/260,007

(22) Filed: Mar. 2, 1999

Related U.S. Application Data

(63) Continuation-in-part of application No. 08/672,244, filed on Jun. 28, 1996, now Pat. No. 5,876,454, which is a continuation of application No. 08/323,023, filed on Oct. 14, 1994, now abandoned, which is a continuation-in-part of application No. 08/226,345, filed on Apr. 12, 1994, now abandoned, which is a continuation-in-part of application No. 08/058, 753, filed on May 10, 1993, now abandoned.

(51) Int. Cl.[7] .............................................. G02N 27/26
(52) U.S. Cl. ....................................... 204/403; 435/817
(58) Field of Search ......................... 204/403; 435/817; 427/2.13

(56) References Cited

U.S. PATENT DOCUMENTS

| 5,443,701 A | * | 8/1995 | Willner et al. ............ 205/777.5 |
| 5,512,489 A | * | 4/1996 | Girault et al. ............ 205/777.5 |
| 5,620,850 A | * | 4/1997 | Bamdad et al. ............. 530/300 |
| 5,942,388 A | * | 8/1999 | Wilner et al. .................. 435/6 |
| 6,060,256 A | * | 5/2000 | Everhart et al. ........... 435/7.21 |

FOREIGN PATENT DOCUMENTS

| DE | 4212912 A1 | * | 10/1993 |
| WO | 9403496 | * | 2/1994 |

OTHER PUBLICATIONS

Scouten et al., Enzyme or protein immobilization techniques for application in biosensor design, Tibtech May 1995 (vol. 13).
Ye et al., Piezoelectric biosensor for detection of *salmonella typhimurium*, J. Food. Sci., 1067–1071 & 1086 1997, Month unknown.
Pritchard et al., Micron–Scale patterning of biological molecules, VCH Verlagsgesellschaft mbH, Weinheim/Bergstr. 1995.
Doretti et al., Covalently immobilized choline oxidase and cholinesterases on a methacrylate copolymer for disposable membrane biosensors, Applied Biochemistry and Biotechnology, vol. 74, 1998, Month unknown.
Wagner et al., Covalent immobilization of native biomolecules onto Au(111) via N–hydroxysuccinimide ester functionalized self–assembled monolayers for scanning probe microscopy, Biophysical Journal, vol. 17 2052–2066 (1996) May.

Fishman et al., Biosensors in Chemical Separations, Annu. Rev. Biophys. Biomol. Struct., 27 165–198 (1998), Month unknown.
Ahluwalia et al., A comparative study of protein immobilization techniques for optical immunosensors, Biosensors & Bioelectronics, 7, 207–214 (1991), Month unknown.
Geddes et al., Immobilisation of IgG onto gold surfaces and its interaction with anti–IgG studied by surface plasmon resonance, Journal of Immunological Methods, 175 149–160 (1994), Month unknown.
JPO abstract of Nakano et al. (JP 02–42984 A).*
CAPLUS abstract of Wagner et al. ("Covalent anchoring of proteins onto gold–directed NHS–terminated self–assembled monolayers in aqueous monolayers in aqueous buffers: SFM images of clathrin cages and triskelia," FEBS Letters (1994), 356(2,3), 267–71).*
CAPLUS abstract of Badia et al. ("Structure and Dynamics in Alkanethiolate Monolayers Self–Assembled on Gold Nanoparticles: A DSC, FT–IR, and Deutrium NMR study," Journal of the American Chemical Society (1997), 119(11), 2682–2692).*
CAPLUS abstract of Taborelli et al. ("Organic monolayers chemisorbed on gold observed scanning probe microscopy," fresenius' Journal of Analytical Chemistry (1996), 354(7–8), 777–8).*
CAPLUS abstract of Duchek et al. ("Monoclonal Antibody––Gold biosensor Chips for Detection of Depurinating Carcinogen–DNA Adducts by Fluorescence Line–Narrowing spectroscopy," Analytcal Chemistry (2000), 72(16), 3709–3716).*
CAPLUS abstract of Hampp et al. ("Thick–film biosensors," Handbook of Sensors and Actuators (1994), 1(Thick Film sensors), 341–56).*

(List continued on next page.)

*Primary Examiner*—Jill Warden
*Assistant Examiner*—Alex Noguerola
(74) *Attorney, Agent, or Firm*—Crowell & Moring LLP

(57) ABSTRACT

The present invention relates to a biosensor which comprises a covalently attached monomolecular biological conjugate layer and a transducing system, wherein the biological conjugate layer has the following structural formula I:

$$—R—X—P \qquad \qquad I$$

wherein,
R is O or S covalently attached via a first covalent bond to the transducing device surface;
X is a linker covalently attached to R via a second covalent bond and selected from a bond, linear or branched chains of 1 to 30 covalently attached atoms of at least C, N, O, Si or S, rings of at least one of C, N, O, Si or S, and a combination thereof; and
P is a biological molecule stably attached to X via a third covalent bond.

10 Claims, 9 Drawing Sheets

OTHER PUBLICATIONS

CAPLUS abstract of Schalkhammer et al. ("New immobilization techniques for the preparation of thin film biosensors," Immobilised Macromol. (1993), 119–39).*

English language translation of Hintsche et al. (DE 4212912 A1).*

Kajiya et al. ("Glucose sensitivity of thiol–modified gold electrodes having immobilized glucose oxidase and 2–aminoethylferrocene", Chem. Lett. (1993), (12), 2107–10).*

CAPLUS abstract of Hintsche et al. (DE 4212912 A1).*

Derwent abstract of Hintsche et al. (DE 421291 A1).*

* cited by examiner

BIOSENSORS COMPRISING A COVALENTLY ATTACHED MONOMOLECULAR BIOLOGICAL CONJUGATE LAYER AND A TRANSDUCING DEVICE

CROSS REFERENCE TO RELATED APPLICATIONS

This application is a continuation-in-part of co-pending application Ser. No. 08/672,244, filed Jun. 28, 1996, now U.S. Pat. No. 5,876,454 which is a continuation of application Ser. No. 08/323,023, filed Oct. 13, 1994, now abandoned, which is a continuation-in-part of application Ser. No. 08/226,345, filed Apr. 12, 1994, now abandoned, which is a continuation-in-part of application Ser. No. 08/058,753, filed May 10, 1993, now abandoned.

BACKGROUND OF THE INVENTION (a) Field of the Invention

The invention relates to biosensors in which a monomolecular biological conjugate layer is attached to a transducing device.

(b) Description of Prior Art

Biosensors are a rapidly emerging technology for detecting and/or measuring the occurrence of biological phenomena or the presence of biological molecules or organisms. A biosensor is any analytical device incorporating a biological material, a biologically derived material or biomimetic intimately associated with or integrated within a physiochemical transducer or transducing microsystem, which may be optical, electrochemical, thermoelectric, piezoelectric or magnetic (Fishman et al., *Annu. Rev. Biophys. Biomol. Struct.*, 27:165–198, 1998). Typical biosensors are formed by attaching a biological molecule, such as an enzyme or an antibody, to a transducer. The biosensor is exposed to an environment in which it is desired to detect bioactivity or a specific biological entity, and signals emitted by the transducer reflect the involvement of the biological molecule in a bioreaction or biointeraction.

Examples of biosensor technology are disclosed in Ahluwalia et al., "A comparative study of protein immobilization techniques for optical immunosensors," *Biosensors & Bioelectronics*, 7:207–214(1991) and Geddes et al., "Immobilisation of IgG onto gold surfaces and its interaction with anti-IgG studied by surface plasmon resonance," *Journal of Immunological Methods*, 175:149–60 (1994).

An important issue in the construction of biosensors is the attachment and immobilization of a biological material in relation to the transducer. If the biological molecule is not attached in proper relation to the transducer or in sufficient amount, then the sensor may not operate satisfactorily. Problems encountered with prior biosensor constructions include maintaining sufficient accessibility, density and/or orientation of the biologically active molecule or organism used in the biosensor. Some sensor designs enclose the bioactive molecule in a matrix or membrane. Such designs tend to restrict the accessibility of the bioactive molecule to the moiety which it is intended to interact with and sense and thereby limit the sensitivity of the resulting sensor. Attempts have also been made to directly attach bioactive molecules to sensors and/or substrates. However, such techniques do not necessarily result in optimum density of the bioactive sensor molecules or in a uniform orientation of the bioactive sensor molecule with the active site or epitope in a properly exposed position for effective interaction with the intended moiety. None of the prior art biosensors is provided with a chemical coating which would promote optimum biochemical interactions reactions at the biosensor/test medium interface, thereby enhancing the sensitivity and usefulness of the biosensor. Consequently, despite the efforts of the prior art, there remains a substantial need for improved biosensor designs.

In various fields, attempts have been made to affix molecules on the surfaces of articles or materials to modify their surface properties. For example, Sukenik, C. N. et al. (J. Biomed. Materials Res., 24:1307–1323, 1990) describes the modulation of cell adhesion by modification of titanium surfaces with covalently attached self-assembled monolayers. Wieserman et al., U.S. Pat. No. 4,788,176 teaches a process for chemically bonding a monomolecular layer of phosphorous- containing material to metal oxide/hydroxide particles to form an active material suitable for use as an absorbent. Rhee et al., U.S. Pat. No. 5,328,955 discloses covalent attachment of collagen to organic polymers and their use with implants. However, none of these documents discloses or suggests the use of bioactive conjugates which include covalently attached biologically active molecules to a biosensor surface in order to enhance the sensitivity and/or usefulness of a biosensor.

SUMMARY OF THE INVENTION

Advances in the immobilization of affinity ligands and innovation in the merging field of bioelectronics have combined to produce revolutionary new detection devices. Affinity electrodes and biosensors are based on the specific interaction between receptors, enzymes, or antibody molecules and their specific target analytes. The application of this technology to measurement systems has created novel analytical detection devices for such diverse fields as diagnostics, therapeutics, process control, waste and environmental monitoring, computer technology, and the kinetic analysis of the interaction of various biological substances.

Common to every device is a support material to which an immobilized affinity ligand is attached. This ligand may be an enzyme that is designed to monitor the presence of its specific substrate in solution. It may be an antibody that can measure its complementary antigen, or an antigen to detect specific antibodies. The affinity ligand may also be any biospecific molecule that interacts with a particular receptor protein (or vice versa). It can even be an immobilized intact living organism (cellular) that can act on specific substances in the solutions with which it comes in contact.

To detect the interaction of these affinity pairs, a functional biosensor needs an electronic transducer that senses the subtle chemical changes that take place between the immobilized ligand and the specific analyte. The detection process may involve the monitoring of electrical effects such as potentiometric changes, amperometric fluctuations, or capacitance differences; optical effects such as light absorption, scattering, or refractive index; changes in density or mass; acoustical effects such as changes amplitude, frequency, or phase of a sound wave; or thermal differences using sensitive calorimeters. The electronic detector then sends its signals an amplification device that also may process and compute the concentration of the analyte in solution. The output and control of these instruments may be as simple as reading a needle gauge on a device such as a pH meter as complex as sophisticated computerized instruments with programmable interfaces.

The principles of biosensor operation have been employed for decades with oscilloscopes designed to monitor slight changes in electrical phenomena. For instance, an olfactory organ such as the antenna of a butterfly can be placed between the input leads of an oscilloscope and used to detect the interaction of olfactory receptors with various volatile substances. In this case, the initial amplifiers of the receptor-ligand interaction are the olfactory nerves that generate action potentials along their length in response to the binding of specific substances. Important qualitative information can be obtained in such a system, but is of little quantitative use.

In modern biosensor design, a synthetic receptor-ligand surface is constructed that has specificity for a single substance. Since the surface is monospecific and the response varies in proportion to the quantity of ligand in the sample solution, quantitative analytical measurements are possible.

The goal is to form a local concentration of the affinity ligand across the biospecific surface. Correct orientation and retention of activity are important in this process, especially for ligands containing active sites that must interact with specific analytes after immobilization.

In general, entrapment or absorption procedures do not yield stable affinity systems for biosensor design. Such sensors may work for brief periods in the laboratory, but the weak bonds created by noncovalent attachment usually cause severe leakage of the biomolecule off the surface and degradation of performance with use. Entrapment, however does provide a viable immobilization means when attaching cellular ligands to a surface, since the cells are typically surrounded by a polymerized or gelatinous membrane and are unable to break free.

The aim of the present invention is to provide biosensors in which a monomolecular biological conjugate layer is covalently attached either directly to a transducing device or to a metal coating on at least one surface of a transducing device.

In accordance with the present invention there is provided for use a monomolecular biological conjugate layer adapted to attach to a metallic transducing device directly or to a transducing device which has a thin coat of metal. The monomolecular biological conjugate layer has the following structural formula I:

  I wherein,
  R is O or S, adapted to be covalently attached to a metallic surface;
  X is selected from a bond, linear or branched chains of 1 to 30 covalently attached atoms selected from the group consisting of C, N, O, Si or S or other linking atoms, rings of 1 to 20 covalently attached atoms selected from the group consisting of C, N, O, Si or S or other linking atoms and a combination of rings and chains of similar composition; and
  P is a covalently-attached biological molecule.

More particularly, in accordance with the present invention, X is selected from one of the following possibilities: a direct bond to a biological molecule; a linear alkyl $C_1$–$C_{30}$ chain, terminated by COOH, $NH_2$, OH, SH or other functional groups chosen to permit covalent linking to a biological molecule; a linear chain consisting of 1–20 atoms of C interspersed with 1–10 atoms of N, O or S, terminated by COOH, $NH_2$, OH, SH or other functional groups chosen to permit covalent linking to a biological molecule; a linear alkylsilyl $SiC_1$–$SiC_{30}$ chain, terminated by COOH, $NH_2$, OH, SH or other functional groups chosen to permit covalent linking to a biological molecule; or rings composed of C and/or N, connected directly to a biological molecule or connected by means of linear chains of C, N, O or S atoms, terminated by COOH, $NH_2$, OH, SH or other functional groups chosen to permit covalent linking to a biological molecule.

The X moiety of the biological conjugate is selected depending on the desired P molecule which is to be attached to a transducing device and also is chosen according to the desired spacing distance of the P molecule from the transducing device. Consequently, this leads to the correct orientation of the biological molecule for sensing and/or measuring purposes.

The preferred X moieties in accordance with the present invention are $C_2$–$C_{12}$ alkyl, which may be substituted or non-substituted, $SiC_3$–$SiC_{12}$, which may be substituted or non-substituted, and 1,3,5-triazine (cyclic $C_3N_3$), which may be substituted or non-substituted.

The X moiety may be substituted with a substituent selected from the group consisting of COOH, $NH_2$, OH, SH, Cl or other groups chosen to permit covalent linking to a biological molecule.

The stably attached biological molecule P includes, but is not limited to, a biological material (such as tissue, microorganisms, whole cells, enzymes, receptors, antibodies or nucleic acids), a biologically derived material or biomimetic. Examples of suitable biological materials include osteopontin, derivatized osteopontin, anti-osteopontin antibodies, bone sialoprotein, bone acidic glycoprotein-75, osteocalcin, osteonectin, bone morphogenetic proteins, transforming growth factors, laminin, type IV collagen, type VIII collagen, enamel proteins (amelogenins and non-amelogenins), anti-amelogenin antibodies, $\alpha_2$HS-glycoprotein, fibronectin, cell adhesion peptides, prostaglandin, serum proteins, glucocorticosteroids (dexamethasone), phosphate, phosphoserine, pyrophosphates, phosphothreonine, phosvitin, phosphophoryn, biphosphonates, phosphonates, phosphatases, sulfonates, sulfates, carboxylates, bone and epithelial proteoglycans, mineral and cell binding peptide sequences such as Arginine-Glycine-Aspartic acid (Arg-Gly-Asp), polyaspartate, and other biological molecules capable of interacting with a biological moiety to be sensed or measured.

In accordance with the present invention there is provided a monomolecular biological conjugate layer adapted to covalently attach to a transducing device of a biosensor.

The biosensor can also be coupled with a chemical separations, for example a chromatographic separation process.

Further, the monomolecular biological conjugate layer of the present invention may form a self-assembling monolayer on the transducing device surface.

In addition to covalently attaching the biological molecule, the monomolecular biological conjugate layer inhibits the contamination of the metal surface of the transducing device.

In accordance with the present invention the expression "metal coat" is intended to mean any transducing device material made of solid metal or of a metal sheet or foil, or a material having at least one side or one surface coated with metal.

More particularly, in accordance with the present invention, the metal surface of the transducer may be any metal to which a suitable oxygen or sulfur atom containing functional group can be covalently attached. If the biosensor is to be used in conjunction with a living organism, for example implanted into a living patient, the metal surface of the transducer should be formed of a medically acceptable metallic material. Suitable metals are known to persons skilled in the art. Examples of suitable metals include titanium, stainless steel, tantalum, Vitallium™, gold, silver, platinum and/or alloys thereof. Titanium is the preferred metallic material.

The modified metal surfaces, as in the present invention, may be used for the micro or nanofabrication of molecular patterns or arrays of molecules, which are herein referred to as "molecular integrated circuit". This form of molecular integrated circuits may have applications in fields such as bioelectronics and molecular electronics.

Another application for the monomolecular biological conjugate layer of the present invention would be in the construct of tips for atomic force microscopy (AFM) and/or for scanning probe microscopy. This would allow the studying of the force or interaction between molecules, where one is attach to a substrate and the other is attached to the tip of AFM.

DETAILED DESCRIPTION OF THE INVENTION

The monomolecular biological conjugate layer of the present invention, once covalently attached to the transducing device of the biosensor, provides a covalent attachment of biological molecules through a carbon chain bridge.

Figure 1:
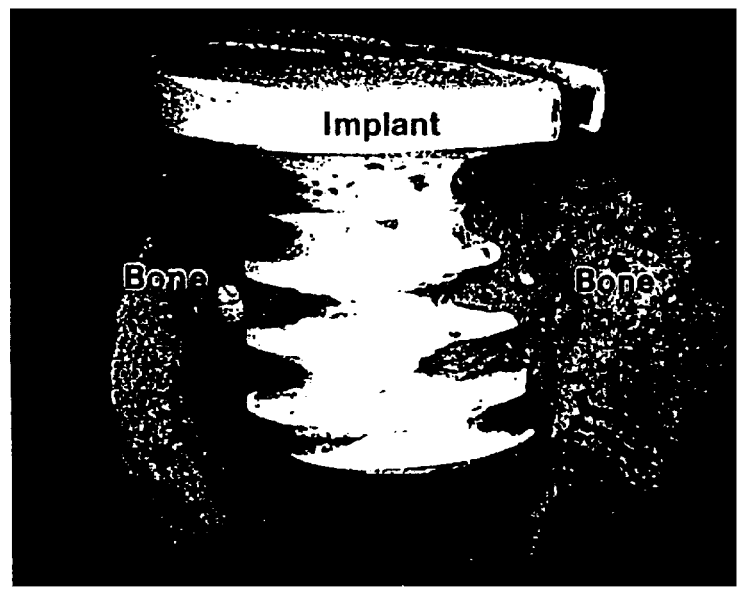
FIG. 1 is a scanning electron micrograph of a titanium screw implant in situ in a rat tibia bone model.

FIG. 1 illustrates the tissue-implant interface of a non-coated implant in situ in bone.

Figure 2:
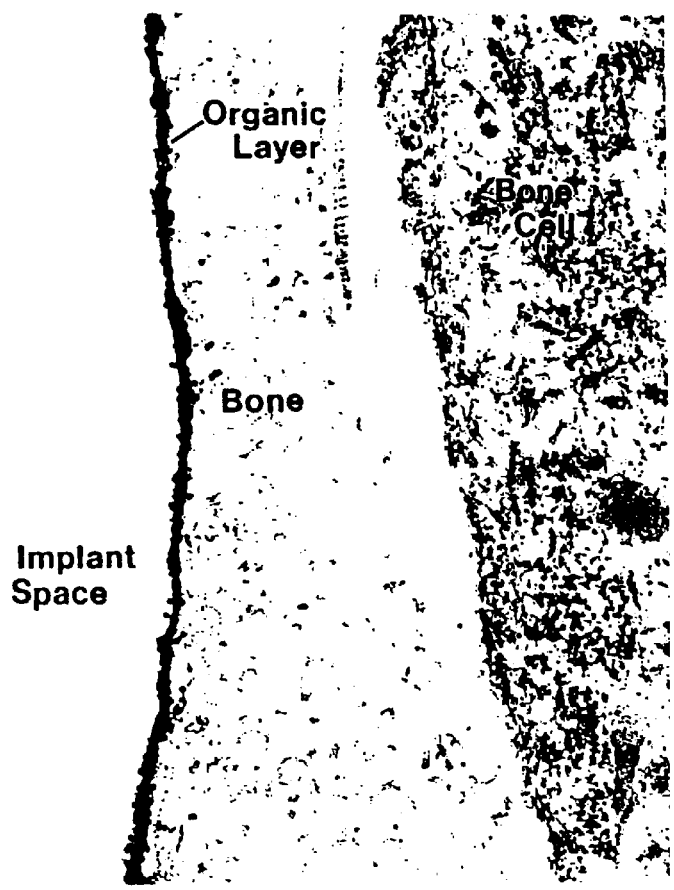
FIG. 2 is a transmission electron micrograph of the tissue-implant interface in a tibial bone showing an accumulation of organic material immunolabeled for the bone protein osteopontin.

A thin layer at the bone-implant interface can be observed at higher magnification by electron microscopy in FIG. 2, which was identified as containing a naturally occurring bone protein known as "osteopontin". Thereafter, in accordance with the present invention, a preferred protein for coating an implant is osteopontin.

Figures 9A, 9B:
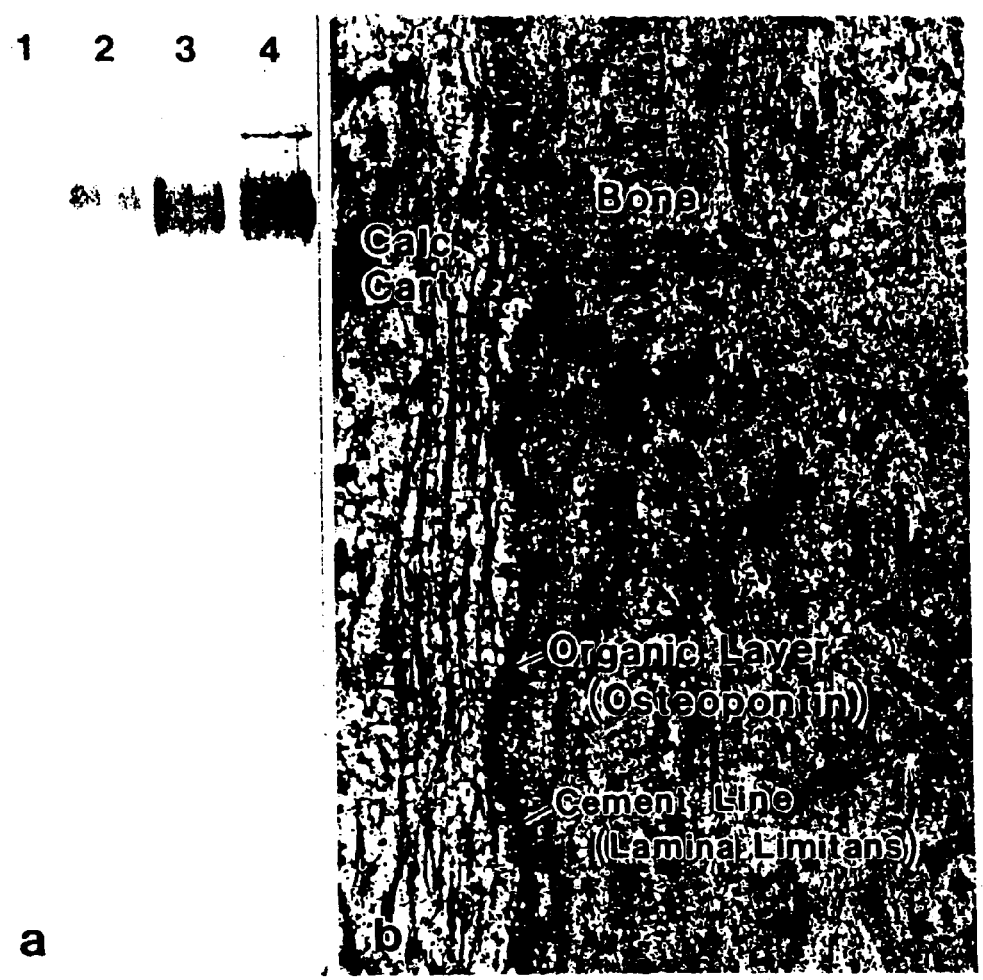
FIG. 9A illustrates an immunoblot with a polyclonal anti-osteopontin antibody raised in chickens and purified from egg yolks.
FIG. 9B illustrates immunocytochemical labeling for rat osteopontin at the interface between calcified cartilage and bone in the rat tibial growth plate using the same anti-osteopontin antibody as used for FIG. 9A.

FIG. 9A illustrates an immunoblot with an antibody against osteopontin raised in chickens and purified from egg yolk. The polyclonal anti-osteopontin antibody was raised against osteopontin purified from rat bone. Lane 1, rat serum albumin; Lane 2, total HCl/guanidine bone extract; Lane 3, purified rat bone osteopontin; Lane 4, purified rat bone osteopontin donated by Drs. M. C. Farach-Carson and W. T. Butler (University of Texas, Houston).

FIG. 9B illustrates immunocyochemical labeling for rat osteopontin in the rat tibia using the anti-osteopontin antibody and demonstrating the concentration of this protein, as visualized by the accumulation of gold particles over an organic layer, referred to as the "cement line" or "lamina limitans" at a natural, matrix-matrix (calcified cartilage-bone) interface as found in normal tissues (McKee et al., Anat. Rec., 234:479–492, 1992; McKee et al., J. Bone Miner. Res., 8:485–496, 1992).

This interface represents the junction between two spatio-temporally distinct matrices created during normal long bone growth where bone is deposited by osteoblasts onto a "scaffolding" of calcified cartilage. During bone remodeling, this same layer of protein is also found at bone-bone interfaces ("cement lines"). It is thus proposed that osteoblasts behave similarly when encountering a titanium "substrate" and secrete an osteopontin-containing, organic layer at the bone-titanium interface (FIG. 10);

FIG. 10 illustrates when a tooth erupts into the oral cavity, part of the reduced enamel organ is believed to fuse with the gingiva to form the functional epithelium (Schroeder and Listgarten, Monographs in Developmental Biology, Ed. A. Wolsky, Tarrytown, N.Y., Vol.2:1–127, 1971). More specifically, the "basal lamina" separating the maturation stage ameloblasts from the enamel surface shows characteristics similar to the internal basal lamina of the junctional epithelium, and may indeed, take part in the formation of the initial epithelial attachment (Nanci et al., Histochemistry, 99:321–331, 1993).

Maturation stage ameloblasts are post-secretory cells which produce little or no enamel proteins, and indeed, the basal lamina separating them from enamel does not seem to contain much of these proteins. However, it is well known that under certain conditions (epithelial pearls; intermediate cementum), epithelial cells related to tooth formation can be reactivated to produce enamel proteins.

Consistent with the epithelial origin of the attachment, cells of the junctional epithelium were examined to determine whether they are able to express enamel proteins. Enamel proteins consist essentially of two classes of proteins, amelogenins and non-amelogenins (enamelins) both of which undergo substantial extracellular processing (reviewed in Nanci and Smith, Calcification in Biological Systems, Chapter 13: 313–343, 1992).

Figures 10A, 10B:
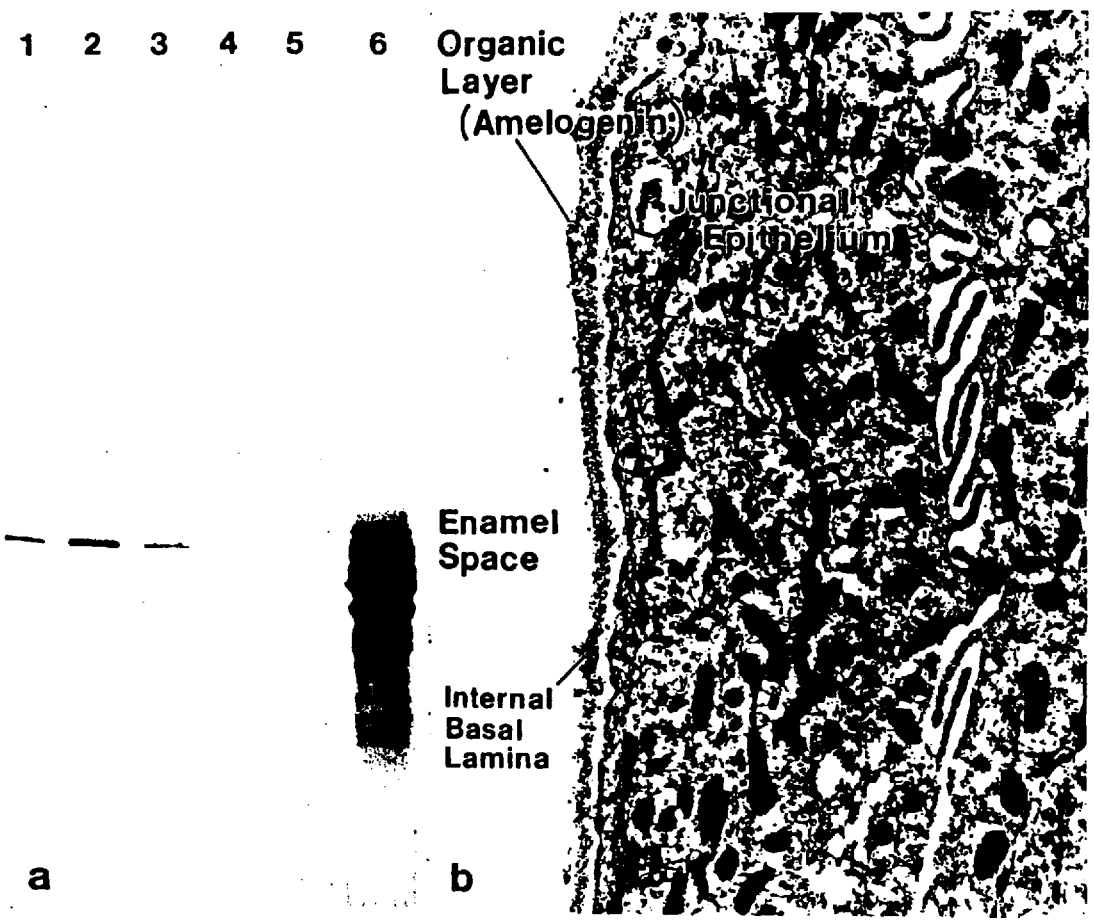
FIG. 10A is an immunoblot of intact proteins and degradation products in enamel organ and enamel matrix using rabbit anti-mouse amelogenin antibody.
FIG. 10B illustrates the immunodetection of enamel proteins in the organic layer between the tooth surface and the junctional epithelium of rat molars.

An antibody raised in rabbits against recombinant mouse amelogenin protein expressed in *E. coli* (courtesy of the laboratory of Dr. H. C. Slavkin, Center for Craniofacial Molecular Biology, University of Southern California) was used to immunolocalize enamel proteins. Proteins from rat incisor enamel were purified, and antibodies to these proteins were raised in the chicken (purified from the egg yolk; in collaboration with Dr. C. E. Smith, McGill University). The rabbit anti-mouse amelogenin recognizes intact proteins and degradation products found between 14 and 31 kDa in ameloblasts (FIG. 10A, lanes 1–5) and enamel matrix (FIG. 10A, lane 6). Maturation stage ameloblasts (FIG. 10A, lanes 3–5) gradually stop producing enamel proteins.

Enamel proteins are immunodetected in the organic layer (internal basal lamina) between the tooth surface and the junctional epithelium of rat molars (FIG. 10B). Since so far it has not been possible to clearly demonstrate the presence of typical basement membrane constituents in the internal basal lamina of the junctional epithelium, or as a matter of fact of in that related to maturation stage ameloblasts, the possibility exists that these basal laminae represent extracellular matrices related to basement membranes but with a distinct composition reflecting their specialized function, such as mediating cell differentiation and/or promoting soft tissue-hard tissue adhesion.

The process, in accordance with the present invention for coating a metal transducing device or a transducing device with a thin metal coating with a monomolecular biological conjugate layer, comprises the following steps.

First, a metal surface is cleaned and deoxidized by effecting a potentiostatic electrochemical polishing in a perchloric acid-butanol-methanol solution similar to that described by M. Volmer-Uebing et al. (Applied Surface Science, 55:19–35, 1992). The preparation of low-oxide metal surfaces at room temperature is by polarizing the metal in 1M perchloric acid ($HClO_4$) at a potential of 40 V. Under these conditions the metal is in a thermodynamically stable phase. The deoxidized surface may then be reoxidized also by potentiostatic electrochemical polarization in a phosphate buffer at 6 V.

Second, the cleaned deoxidized or controlled re-oxidized metal surface is contacted with compounds that cause covalent attachment with the monomolecular biological conjugate layer of the present invention.

Theoretical Coverage of Surface with Sulfur
a) perfect crystal (flat surface)

The surface concentration of titanium (Ti) is about $1.6 \times 10^{15}$ atoms/cm$^2$ and the diameter of sulfur (S) is about 2×diameter of Ti, thus the surface concentration of sulfur atoms is about $0.8 \times 10^{15}$ atoms/cm$^2$ and each sulfur atom is attached to a chain of 18 carbon atoms of about 15 Å long.

Because the depth analyzed is 45 Å, the surface concentration of carbon atoms is about $1.4 \times 10^{16}$ atoms/cm$^2$, that is about 18 times the surface concentration of sulfur atoms).

Depth probed (≈45 Å)–length of thiolase (≈15 Å)=30 Å
30 Å Ti ≈11 monolayers ≈$1.8 \times 10^{16}$ atoms/cm$_2$
Ti:S:C=$1.8 \times 10^{16}$:$0.8 \times 10^{15}$:$1.4 \times 10^{16}$=54.9%:2.4%:42.7%
b) 45° sawtooth surface (rough surface, more realistic)
Ti:S:C=41.6%:2.8%:55.6%
c) contaminated surface Since titanium (Ti) is a reactive metal, it is difficult to clean and it gets recontaminated easily.

The realistic coverage of the Ti surface with S is less than 2.8%, this value depends on the extent of the contamination of the surface.

TABLE 1

Atomic percentages at reduced titanium surfaces following treatment with a functionalized alkanethiol

| Treatment | O | Ti | C | S |
|---|---|---|---|---|
| SH(CH$_2$)$_2$COOH | 35.7 | 7.3 | 53.9 | 2.1 |
| SH(CH$_2$)$_2$COOH/H$_2$O | 43.2 | 15.4 | 37.2 | 2 |

Table 1 above provides a comparison of chemically-treated reduced titanium surfaces before and after aqueous exposure.

Figure 11:
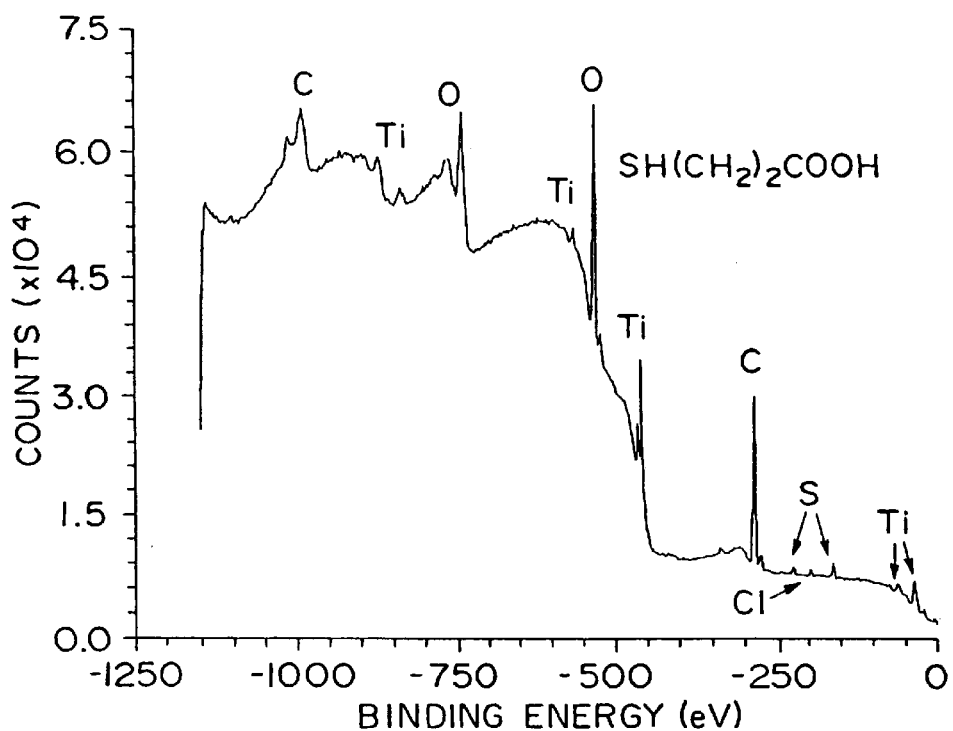
FIG. 11 is an XPS spectrum showing the presence of sulfur at the reduced titanium surface after treatment with a functionalized short-chain alkanethiol.

FIG. 11 demonstrates sulfur peaks indicating thiol binding to titanium.

Figure 12:
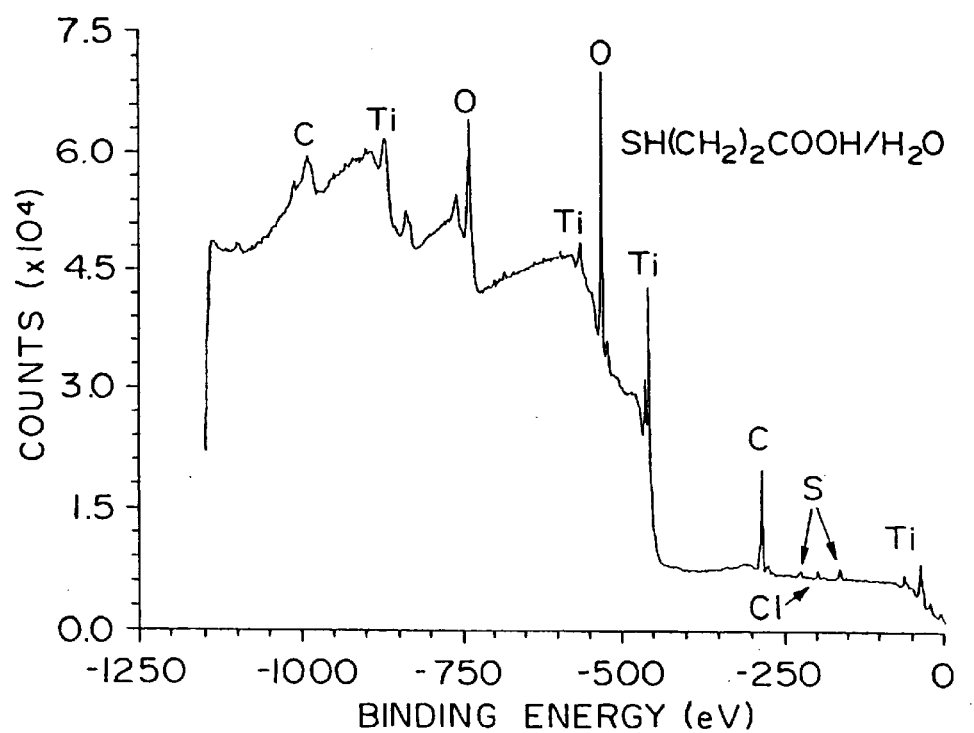
FIG. 12 is an XPS spectrum showing retention of sulfur and stability of the Ti—SH bonding following exposure of the alkane-treated titanium surface to water.

FIG. 12 shows no major change in the sulfur (thiol) peaks after aqueous treatment.

The present invention will be more readily understood by referring to the following examples which are given to illustrate the invention rather than to limit its scope.

EXAMPLE I

Coating of a Titanium Metal Substrate with Octadecyl Thiolate

Sample Preparation

The titanium metal substrate is cleaned by mechanical polishing with alumina 0.1 μm followed by an ultrasonic chemical cleaning in pure acetone for about 15 min. The substrate is electrochemically polished in a perchloric acid-butanol-methanol solution in a 1:12:7 ratio by volume for 30 min. at about 40 V. This technique establishes the electrochemical conditions at which the surface contaminants are unstable, and are removed. Although no attempt was made in this experiment to the experimental conditions, the technique as used, caused a measurable cleaning of the titanium surface.

The cleaning was carried out in a $N_2$-flushed dry box which also contains $10^{-3}$ to $10^{-4}$M hexane solutions of octadecyl thiol, $CH_3$—$(CH_2)_{17}$—SH. Thus, without exposure to air, which is capable of re-contaminating the highly reactive clean titanium surface, the metal was submerged in the thiol solution overnight. This permitted the thiol to react with the metal surface, forming self-assembling monolayers, such as

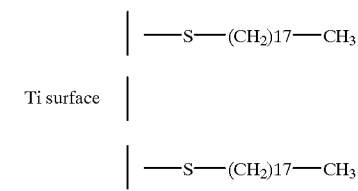

which extend above the metal surface by about 15 Angstroms. Samples were rinsed in hexane before analysis.

Analysis Technique

The surface analytical technique used is called X-ray Photoelectron Spectroscopy (XPS) or Electron Spectroscopy for Chemical Analysis (ESCA). It has the advantage that small differences in electron density at the emitting atom, caused by differences in chemical bonding, are reflected in small shifts in the energy of the emitted electron. Software has been developed which permits the computer manipulation of these data, allowing the separation of close-lying peaks for further study.

The depth probed at the titanium emission energy is about 45 Angstroms; for a perfectly flat titanium crystal covered with a monolayer of thiol, the depth probed into the titanium is, then, about 30 Angstroms. For a rougher surface, modeled on a 45° saw-tooth, this depth is closer to 20 Angstroms although the full thiolate monolayer is probed in both cases.

Results and Discussion

Figure 3:
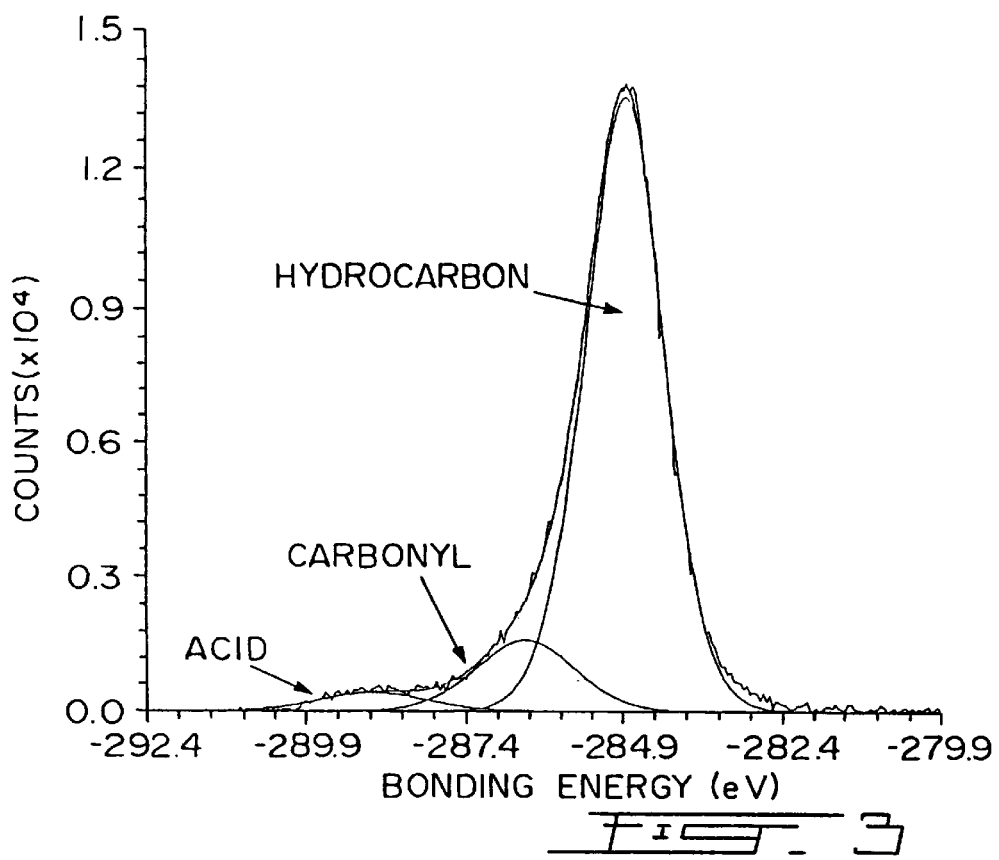
FIG. 3 represents the carbon spectrum obtained by X-ray Photoelectron Spectroscopy of the surface of a titanium implant which has reacted with a hexane solution of octadecyl thiol, showing the octadecyl thiolate attached thereto.
Figure 4:
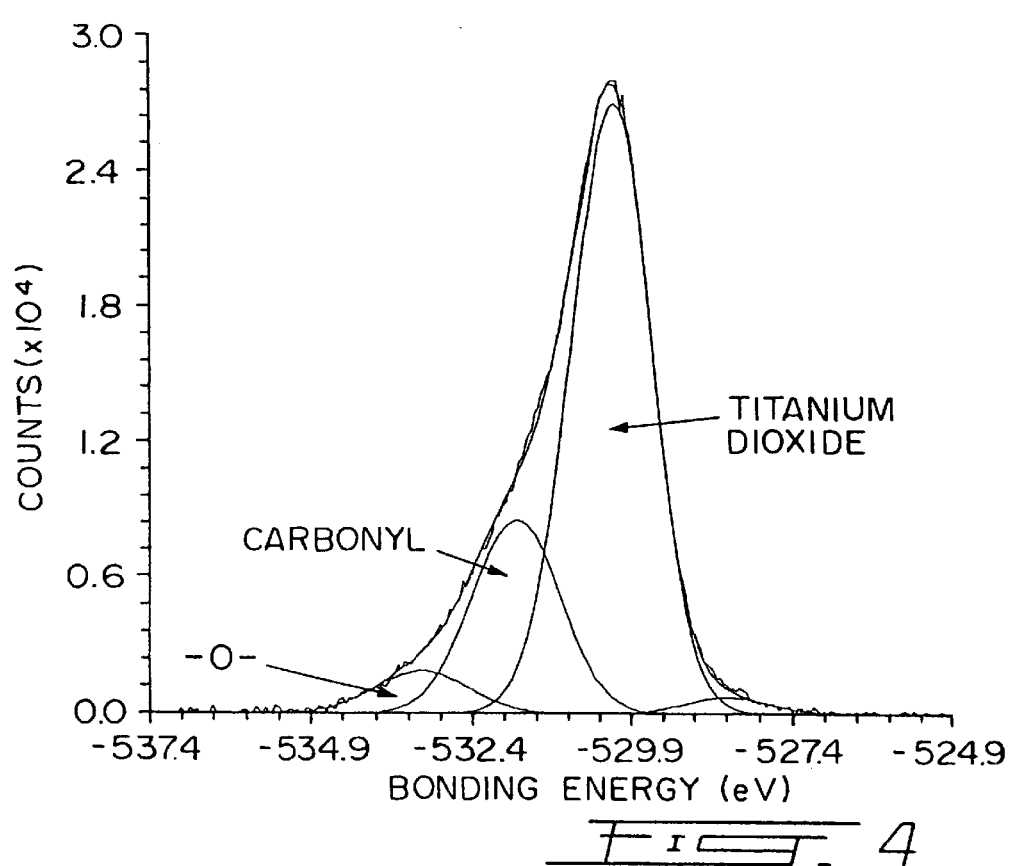
FIG. 4 represents the oxygen spectrum obtained by X-ray Photoelectron Spectroscopy of the surface of a titanium implant with octadecyl thiolate attached thereto.
Figure 5:
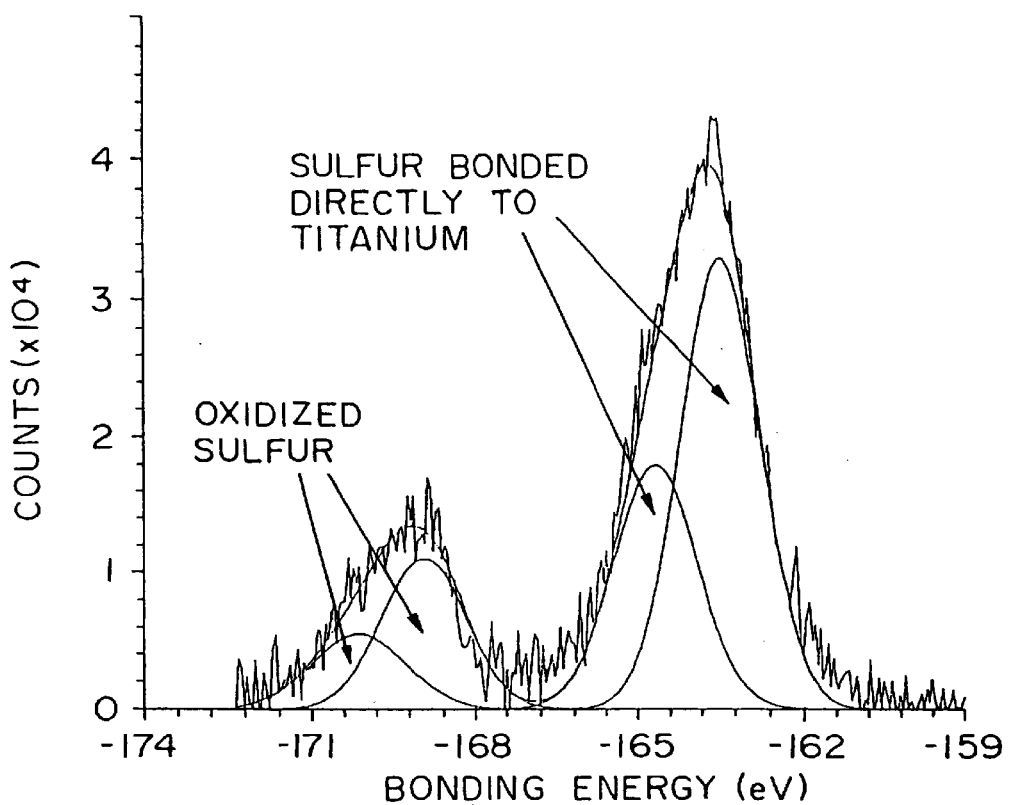
FIG. 5 represents the sulfur spectrum obtained by X-ray Photoelectron Spectroscopy of the surface of a titanium implant with octadecyl thiolate attached thereto.
Figure 6:
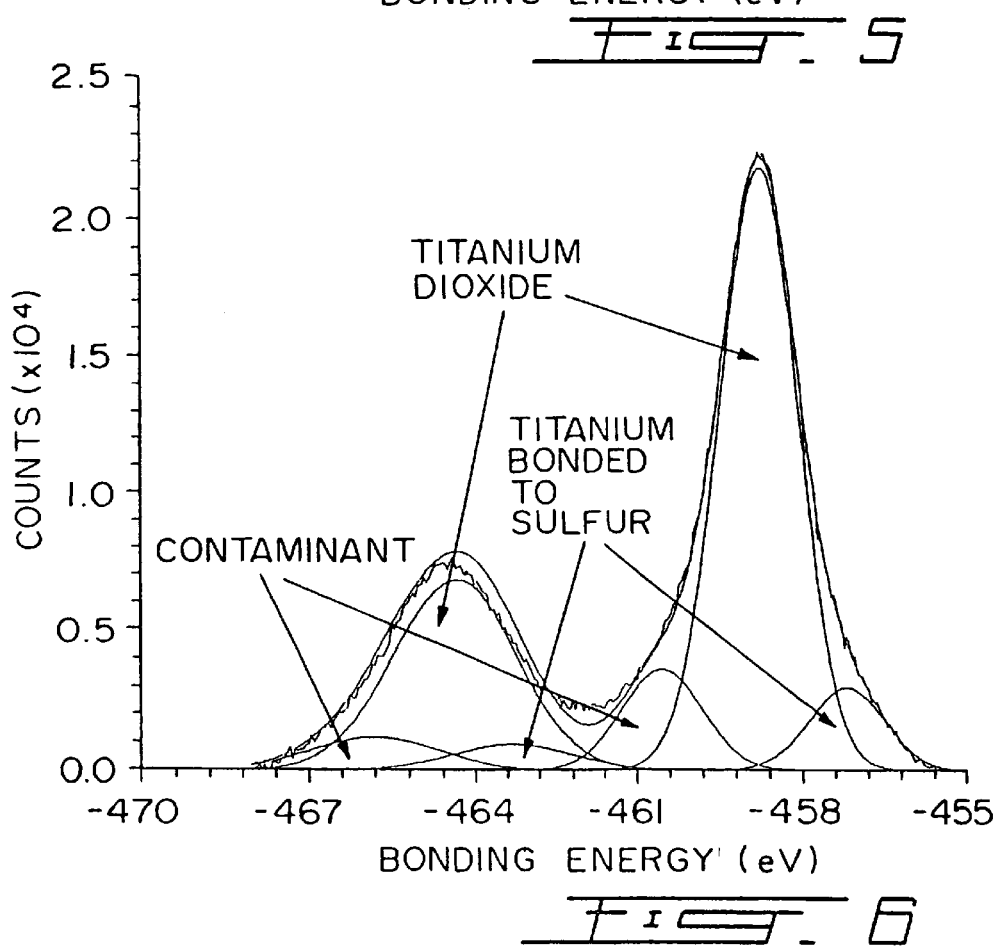
FIG. 6 represents the titanium spectrum obtained by X-ray Photoelectron Spectroscopy of the surface of a titanium implant with octadecyl thiolate attached thereto.

A typical set of spectra is seen in the accompanying FIGS. 3 to 6, where FIG. 3 is the carbon spectrum, FIG. 4 is the oxygen spectrum, FIG. 5 is the sulfur spectrum and FIG. 6 is the titanium spectrum. The peaks for carbon and oxygen arise from electrons emitted from s-type orbitals, meaning that each peak indicates another environment. Their probable attributions are indicated on the FIGS. 3 and 4.

On the other hand, the peaks for sulfur and titanium arise from electrons emitted from p-type orbitals, meaning that pairs of peaks indicate different environments. Again, probable attributions are indicated on the FIGS. 5 and 6.

The fact that titanium can clearly be detected indicates that only a monolayer of thiol was deposited. Variations in carbon and oxygen percentages, as well as in the various titanium components, indicates some point-to-point variability in cleaning and thiol deposition. However the thiol directly bonded to titanium appears impervious to attack by water vapor and by direct water immersion for at least 2.5 hours.

EXAMPLE II

Covalent Attachment with Thiol of Alkaline Phosphatase to a Titanium Metal Surface A cleaned titanium metal surface is coated with 16-aminohexadecanethiol by the general procedure described in Example I. The metal is then stirred for 60 min. at 25° C. under $N_2$ with a solution of glutaraldehyde in 0.1 M phosphate buffer. The metal is then rinsed with buffer and stirred for 12 hours at 25° C. with a solution of 3 mg alkaline phosphatase (from bovine intestinal mucosa, 5 units/mg) in 3 mL phosphate buffer. The metal is then rinsed with buffer. Enzymatic activity would be measured by the method of Lowry et al. (J. Biol. Chem., 164:321, 1946).

EXAMPLE III

Covalent Attachment with Silane of Alkaline Phosphatase to a Titanium Metal Surface A titanium metal surface was cleaned by the general procedure of Example I and subjected to controlled re-oxidation. The metal was then stirred for 2 hours under $N_2$ with a 10% solution of 3-aminopropyltriethoxysilane in refluxing toluene. The modified metal was then covalently coupled with alkaline phosphatase by the glutaraldehyde procedure described in Example II. Enzymatic activity was measured by the method of Lowry et al. (J. Biol. Chem., 164:321, 1946).

Figure 7:
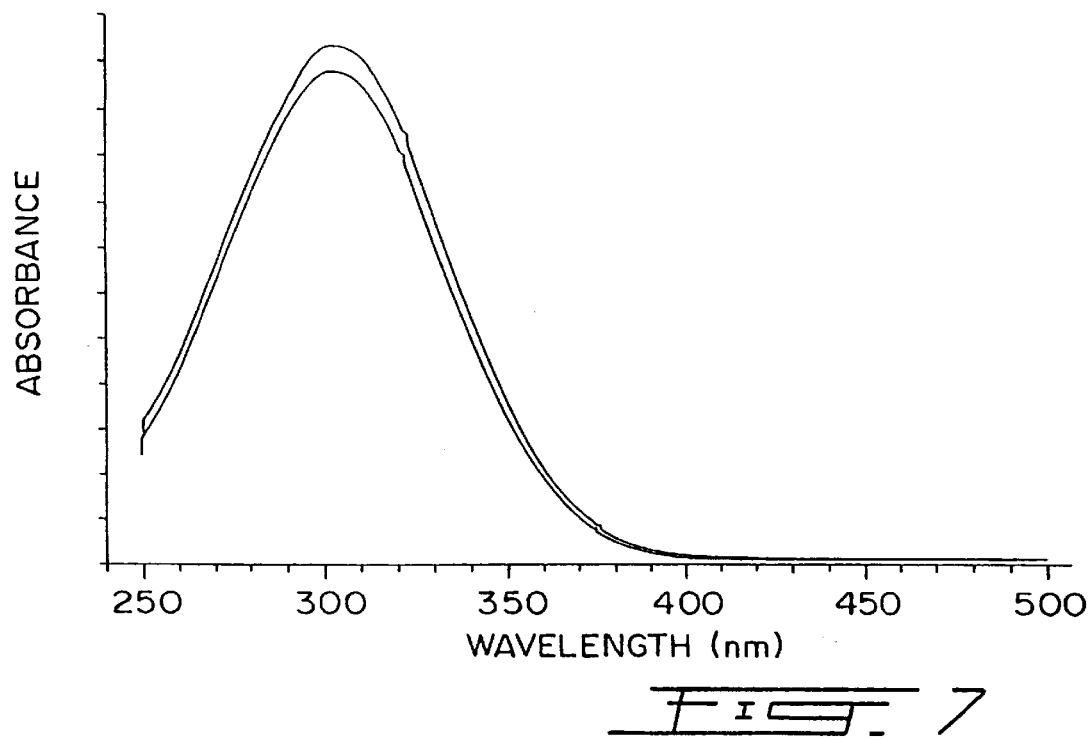
FIG. 7 is a UV spectrum showing initial evidence of the biological activity of a bioactive conjugate coating an implant prepared according to the present invention.
Figure 8:
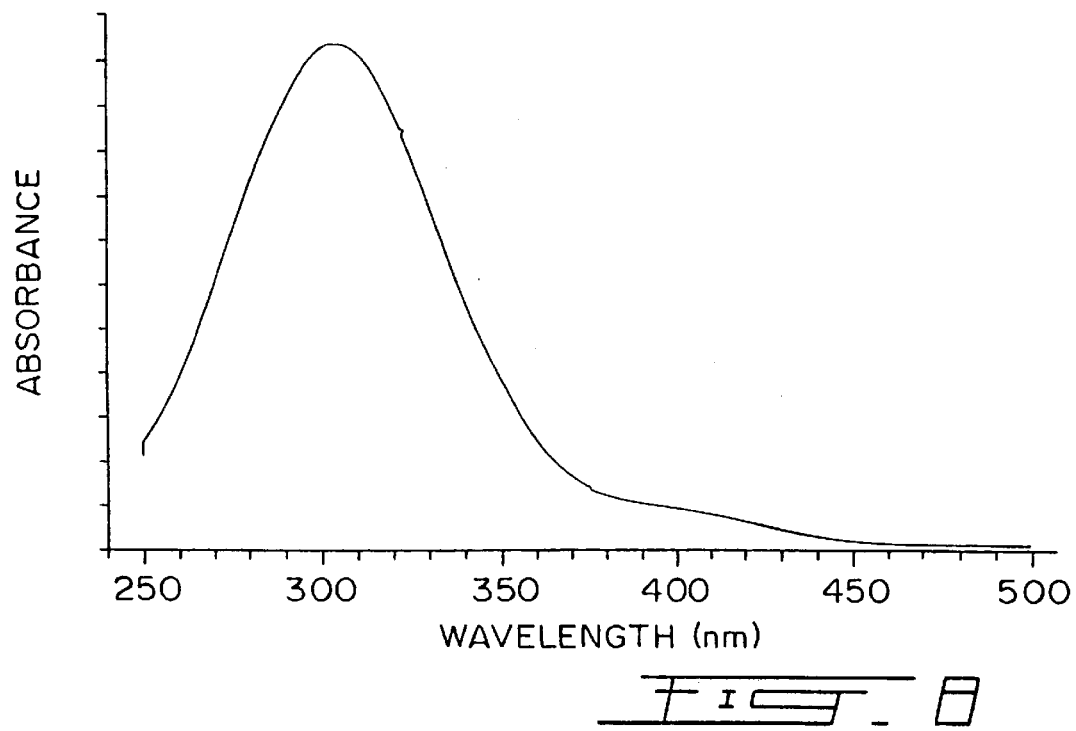
FIG. 8 is a UV spectrum showing evidence of the biological activity of the bioactive conjugate coating the implant after 14 hours of incubation.

FIG. 8 shows the appearance of a peak at 405 nm which provides clear evidence the alkaline phosphatase covalently-attached to an implant surface has retained its biological activity after 14 hours of incubation. Although, the peak at 405 nm is essentially absent from FIG. 7 which is taken near the beginning of the reaction, weak absorbance at 405 nm indicates initial stages of formation of p-nitrophenol by enzyme-catalysed hydrolysis.

EXAMPLE IV

Covalent Attachment of Alkaline Phosphatase to $TiO_2$

A sample of powdered $TiO_2$ was stirred for 2 hours under $N_2$ with a 10% solution of 3-aminopropyl-triethoxysilane in refluxing toluene. After centrifugation, rinsing with toluene, and drying, the modified $TiO_2$ was stirred for 60 min. at 25° C. under $N_2$ with a 2.5% solution of glutaraldehyde in 0.1 M phosphate buffer.

After centrifugation and rinsing with 0.1 M buffer, the modified $TiO_2$ was stirred for 12 h. at 25° C. with a solution of 3 mg alkaline phosphatase (from bovine intestinal mucosa, 5 units/mg) in 3 mL phosphate buffer. The modified $TiO_2$ was then rinsed thoroughly with buffer, and its enzymatic activity was measured by the method of Lowry et al. (J. Biol. Chem., 164:321, 1946).

Figure 13:
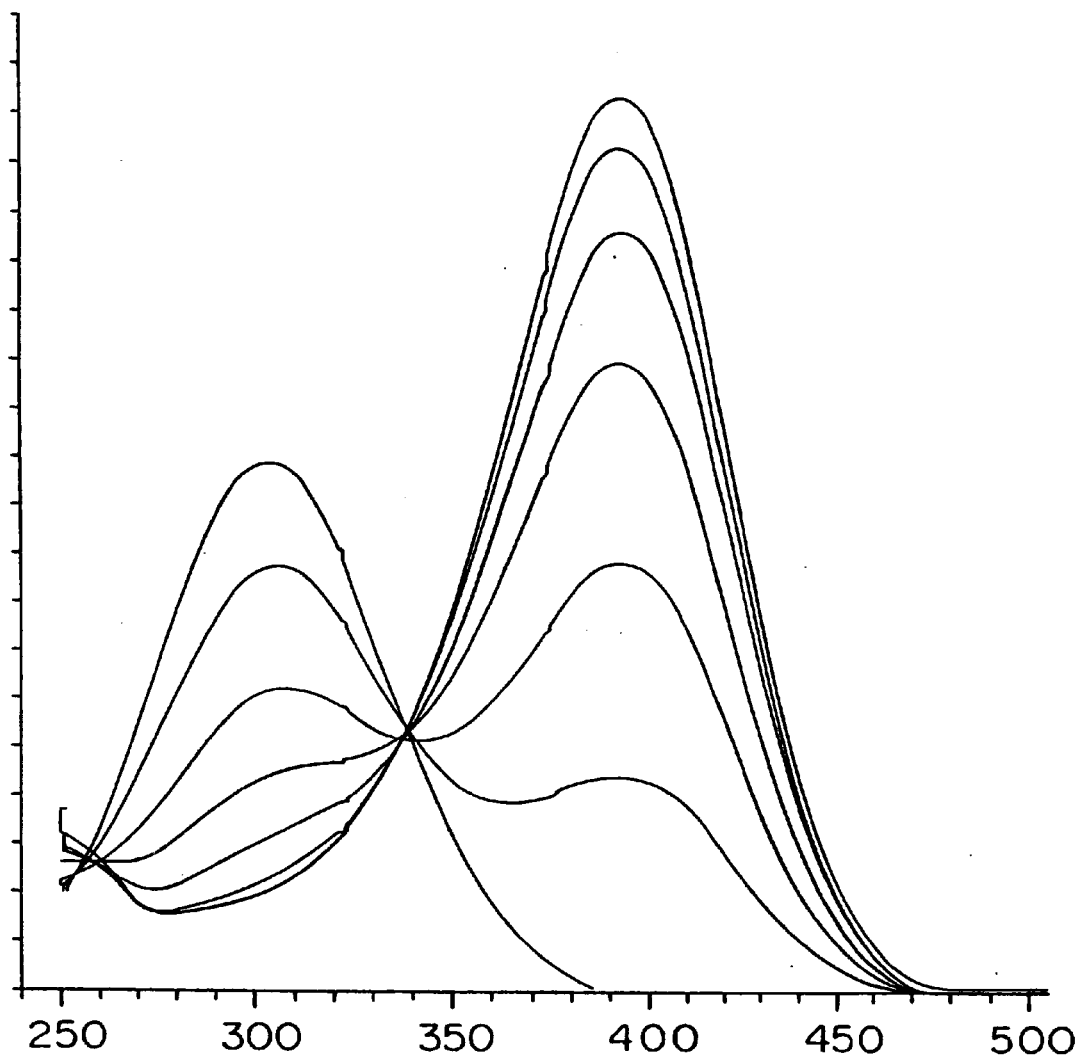
FIG. 13 represents a series of seven UV spectra of the surface of a titanium implant with alkaline phosphatase attached thereto.

FIG. 13 shows a series of seven UV spectra taken at 15 min. intervals from t=0 to t=90 min. during the course of an assay of a sample of modified $TiO_2$ using the method of Lowry. The peak near 305 nm, which corresponds to unhydrolyzed p-nitrophenyl phosphate, decreases continuously and is essentially absent at t=90 min. There is a corresponding increase in absorption near 395 nm, which corresponds to the formation of p-nitrophenolate. These spectra provide clear evidence for covalent attachment of alkaline phosphatase to $TiO_2$ in an enzymatically active form.

Figures 14A, 14B:
FIG. 14A illustrates a junctional epithelial cell in contact with surgically-exposed dentin showing the presence of enamel proteins (gold particles, arrowheads) interposed between the cell and the exposed dentin.
FIG. 14B is a micrograph illustrating a layer of osteopontin (gold particles, arrowheads) separating exposed dentin and a (pre)cementoblast.

For examining tissue repair and the production of new proteins at exposed mineralized tissue surfaces, we have used a model where the junctional epithelium is surgically detached (reflected) from the tooth surface and the palatal root of rat molars is exposed and the cementum and outer-most dentin is removed from the root surface with a dental bur. Tissue healing in this circumstance occurs soon thereafter and comprises both a soft and hard tissue response in which two principal events occur. First, junctional epithelium migrates down the tooth and over the damaged root surface and re-establishes an epithelial attachment. Coincident with the contact of these epithelial cells to the exposed dentin and/or cementum, enamel proteins (as indicated by immunoreactivity to antibodies raised against this epithelial secretory product) are secreted and accumulate as an organic layer at the root surface (FIG. 14A) adjacent to junctional epithelial cells. This class of protein is generally not believed to be expressed after completion of the enamel layer in unerupted teeth yet has here been shown to be part of the normal epithelial attachment (see FIG. 10B) and to be produced during reparation of this epithelial structure. Second, with regard to hard tissue formation and healing at these damaged sites in regions more apical to the epithelial cell migration, (pre)cementoblast are found against the tooth surface and are associated with the appearance of a layer of osteopontin (FIG. 14B) at the exposed root surface. This organic coating of osteopontin appears to be the initial event of reparative cementogenesis in which typical cementum then begins to fill in the defect at the root surface.

EXAMPLE V

Microfabrication

The synthesis of arrays of molecules on the planar metal surface of the present invention essentially relies on three fundamental processes: (1) covalent immobilization of molecules at a metal surface in accordance with the present invention; (2) in situ synthesis of molecules on the surface (self-assembly); and (3) physical entrapment of molecules in defined areas. Each of these processes can be scaled to micro- or nanometer dimensions.

The technology currently used for the fabrication of "molecular integrated circuits" can readily be adapted for molecular patterning at the micrometer scale. If specific electrochemical interaction or electrical signal measurement is required within a molecular array, then microelectrodes can be used as the molecular attachment sites. Alternatively, the lithographic techniques developed for integrated-circuit fabrication in the electronics industry can be adapted to pattern molecules and create "molecular integrated circuits".

The term "microelectrode" when used herein, is intended to mean any device which is derived from semiconductor technology but which is able to function in a physiological environment for electrical measurements at the cellular level in vitro or in vivo. Such microelectrodes, which may be used in accordance with the present invention, include 1) a metal, e.g. titanium, microelectrode cleaned and coated as described above; or 2) a microelectrode of the prior art coated with a thin layer of metal, e.g. titanium, which is then cleaned and coated as described above. Thus, in accordance with the present invention, the microelectrodes are not coated using polymers as opposed to the prior art techniques. Accordingly, the microelectrodes of the present invention, because they do not include polymers, present the advantage of direct attachment and precise orientation of molecules.

A cleaned metal surface prepared according to the general procedure described in Example I can be used as an electrode for the preparation of such micro- or nanofabricated molecular integrated circuits or molecular arrays.

Photolithography enables the creation of devices or arrays to dimensions of ~2 μm in most clean-room facilities by the patterning and development of standard photoresists on planar surfaces. Dimensions smaller than this (to ~0.3 μm) can be achieved with more sophisticated optical lithography techniques currently used for the commercial synthesis of microelectronic chips (reviewed by P. Connolly, *TIBTECH*, 12:123–127, April 1994).

These devices are able to function in a physiological environment. For individual measurements at the cellular level, a suitable microelectrode should have dimensions on the order of a few micrometers, and most designs conform to this scale.

Another use of microelectrode-polymer arrays is the localized immobilization of molecules which are available for repetitive or successive interactions with cellular receptors or other molecules and which may trigger biochemical reactions as long as they remain immobilized. This may be used as a system in replacement of a controlled release system of drugs in situ, since the immobilized molecule of the present invention is available for more than one interaction and is an equivalent to the controlled release system.

Another application for the monomolecular biological conjugate layer of the present invention would be in the construct of tips for atomic force microscopy (AFM) and/or for scanning probe microscopy. This would allow the studying of the force or interaction between molecules, where one is attach to a substrate and the other is attached to the tip of AFM.

Further details of procedures for constructing tips for AFM and/or for scanning probe microscopy include a method for the covalent binding of self-assembled monolayers of native biomacromolecules on flat gold surfaces for scanning probe microscopy as described in Wagner et al., *Biophysical J.*, 70:2052–2066 (1996).

EXAMPLE VI

Biosensor

The present invention pertains to biosensors which comprise a covalently attached monomolecular biological conjugate layer and a transducing device. The transducing device includes, but is not limited to, a physiochemical transducer or transducing microsystem, which may be optical, electrochemical, thermoelectric, piezoelectric or magnetic. The monomolecular biological conjugate layer has the following structural formula I:

$$—R—X—P \qquad\qquad I$$

wherein,

R is O or S covalently attached via a first covalent bond to a transducing device surface;

X is a linker covalently attached to R via a second covalent bond and selected from a bond, linear or branched chains of 1 to 30 covalently attached atoms of at least C, N, O, Si or S, rings of at least one of C, N, O Si or S, and a combination thereof; and P is a biological molecule stably attached to X via a third covalent bond.

The stably attached biological molecule P can be any target molecule or compound that interacts specifically with a biological system. A measurable response occurs when a specific interaction takes place between the attached biological molecule and the analyte. P includes, but is not limited to, a biological material (such as tissue, microorganisms, whole cells, enzymes, receptors, antibodies or nucleic acids), a biologically derived material or biomimetic. The biosensor can also be coupled to chemical separations (reviewed in Fishman et al., *Annu. Rev. Biophys. Biomol. Struct.*, 27:165–198, 1998).

The transducing device for the biosensor can be a microelectrode. The microelectrode can be made of a medically acceptable metallic material such as, but not limited to, titanium, stainless steel, tantalum, Vitallium™, gold, silver, platinum and alloys thereof. Alternatively, the microelectrode can have thin layer of metal coating. The metal can be made of a medically acceptable metallic material such as, but not limited to, titanium, stainless steel, tantalum, Vitallium™, gold, silver, platinum and alloys thereof.

Titanium is the preferred metallic material because it is resistant to corrosion and has good electrochemical and biomechanical properties.

A cleaned metal surface can be prepared according to the general procedure described in Example I.

Further details of procedures for constructing biosensors include a method for the direct binding of a protein to metal surfaces in surface plasmon resonance biosensors as described in Geddes et al., *J. Immunol. Methods*, 175:149–160 (1994); a method for covalent coimmobilization of choline oxidase and cholinesterases (acetylcholinesterase and choline oxidase) in 2-hydroxyethylmethacrylate-glycidyl methacrylate disposable membranes and for their use to assemble amperometric sensors as described in Doretti et al., *Appl. Biochem. Biotech.*, 74:1–12 (1994), and two alternative techniques for immobilizing antibodies onto gold electrode coated quartz crystal surfaces as described in Ye et al., *J. Food Sci.*, 62:1067–1071 & 1086 (1997). The first technique described by Ye et al. is dithiobis-succinimidyl propionate (DSP) coupling. In the second, the crystal is pre-coated with a thin layer of polyethyleneimine and activated with glutaraldehyde, the proteins are then attached to the surface through amino groups.

From the information provided in these references, one skilled in the art can construct biosensors which comprise the monomolecular biological conjugate layer of the present invention and a transducing device.

REFERENCES

The following documents provide additional technical information relating to the construction and use of biosensors and are hereby expressly incorporated in this application by reference:

Ahluwalia et al., "A comparative study of protein immobilization techniques for optical immunosensors," *Biosensors & Bioelectronics*, 7:207–214(1991);

Doretti et al., "Covalently Immobilized Choline Oxidase and Cholinesterases on a Methacrylate Copolymer for Disposable Membrane Biosensors," *Applied Biochemistry and Biotechnology*, 74:1–12 (1998);

Fishman et al., "Biosensors in Chemical Separations," *Annu. Rev. Biophys. Biomol. Struct.*, 27:165–98 (1998);

Geddes et al., "Immobilisation of IgG onto gold surfaces and its interaction with anti-IgG studied by surface plasmon resonance," Journal of Immunological Methods, 175:149–60 (1994);

Jianming et al., "Piezoelectric Biosensor for Detection of *Salmonella typhimurium*," *Journal of Food Science*, 62(5):1067–71 (1997);

Pritchard et al., "Micron-Scale Patterning of Biological Molecules," *Angew. Chem. Int. Ed. Engl.*, 34(1):91–92 (1995);

Scouten et al., "Enzyme or protein immobilization techniques for applications in biosensor design," *TIBTECH*, Vol 13, pages (May 1995).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A biosensor comprising a covalently attached monomolecular biological conjugate layer and a transducing device, wherein the biological conjugate layer has the following structural formula I:

—R—X—P    I wherein,

R is O covalently attached via a first covalent bond to the transducing surface;

X is a linker covalently attached to R via a second covalent bond and selected from a bond, linear or branched chains of 1 to 30 covalently attached atoms of a least C, N, O, Si or S, rings of at least one of C, N, O, Si or S, and a combination thereof; and P is a biological molecule stably attached to X via a third covalent bond or a functional group.

2. The biosensor of claim 1, wherein X is a bond, a linear alkyl $C_1$–$C_{30}$ chain, a linear chain consisting of from 1 to 20 C atoms interspersed with from 1 to 10 atoms of N, O or S, a ring composed of C and/or N, or a ring composed of C and/or N connected to a linear chain of C, N, O or S atoms, and X is terminated by a functional group which permits covalent linking to P.

3. The biosensor of claim 2, wherein the functional group is selected from the group consisting of COOH, $NH_2$, OH and SH.

4. The biosensor of claim 1, wherein said biological conjugate forms a self-assembling monomolecular layer.

5. The biosensor of claim 1, wherein the transducing device is a physiochemical transducer.

6. The biosensor of claim 1, wherein the transducing device is selected from the group consisting of optical transducers, electrochemical transducers, thermoelectric transducers, piezoelectric transducers, and magnetic transducers.

7. The biosensor of claim 1, wherein the transducing device is a microelectrode.

8. The biosensor of claim 7, further comprising a thin layer of metal coating the microelectrode, wherein said metal is selected from the group consisting of titanium, stainless steel, tantalum, Vitallium™ and an alloy thereof.

9. The biosensor of claim 1, wherein P is selected from the group consisting of biological tissue, microorganisms, whole cells, enzymes, receptors, antibodies and nucleic acids.

10. The biosensor of claim 1, wherein P is selected from the group consisting of osteopontin derivatized osteopontin, bone sialoprotein, bone acidic glycoprotein-75, osteocalcin, osteonectin, bone morphogenetic proteins, transforming growth factors, laminin, type IV collagen type VIII collagen, enamel proteins (amelogenins and non-amelogenins), $\alpha_2$HS-glycoprotein, fibronectin, cell adhesion peptides, prostaglandin, serum proteins, glucocorticosteroids (dexamethasone), phosphate, phosphoserine, pyrophosphates, phosphothreonine, phosvitin, phosphophoryn, biphosphonates, phosphonates, phosphatases, sulfonates, sulfates, carboxylates, bone and epithelial proteoglycans, mineral and cell binding peptide sequences such as Arginine-Glycine-Aspartic acid (Arg-Gly-Asp), polyaspartate, and other biological molecules capable of interacting with a biological moiety to be sensed or measured.

* * * * *